United States Patent
Ralph et al.

[19]

[11] Patent Number: 5,888,204
[45] Date of Patent: *Mar. 30, 1999

[54] ACETABULAR CUP HAVING CAPPED POLYAXIAL LOCKING SCREWS

[75] Inventors: James D. Ralph, Oakland; Steven Tatar, Montville, both of N.J.

[73] Assignee: Fastenetix, LLC, Summit, N.J.

[ * ] Notice: The term of this patent shall not extend beyond the expiration date of Pat. No. 5,607,426.

[21] Appl. No.: 843,972

[22] Filed: Apr. 17, 1997

Related U.S. Application Data

[63] Continuation-in-part of Ser. No. 632,560, Apr. 15, 1996, Pat. No. 5,725,588.

[51] Int. Cl.⁶ ........................................... A61B 17/56
[52] U.S. Cl. ................................. 623/22; 606/73
[58] Field of Search .................. 606/61, 60, 69, 606/70, 71, 72, 73; 623/16, 22, 23

[56] References Cited

U.S. PATENT DOCUMENTS

| | | | |
|---|---|---|---|
| 4,936,861 | 6/1990 | Muller et al. | 623/22 |
| 5,376,125 | 12/1994 | Winkler | 623/23 |
| 5,607,426 | 3/1997 | Ralph et al. | 606/61 |

*Primary Examiner*—Guy V. Tucker
*Attorney, Agent, or Firm*—Joseph P. Errico, Esq.

[57] ABSTRACT

The present invention is an acetabular cup having at least one polyaxial locking screw for anchoring the cup in the desired bone site. The assembly includes an acetabular cup having at least one through hole having both threaded and tapered portions, into which holes a two-piece interlocking coupling element and a bone screw having a semi-spherical head may be inserted. The two-piece coupling element, including slideably joined socket and cap portions, is mounted about the semi-spherical head of the bone screw, which is inserted into the through hole and into the bone. The head of the screw is polyaxially mounted in the socket portions and as such may be inserted into the bone at a variety of angles. The socket portion of the coupling element has slots which permits crush locking of the head of the screw once the socket seats and is forceably driven into the tapered portion of the hole. The cap portion is threaded so is may be advanced into the inner portion of the hole, thereby further locking the coupling element into the hole, and applying an additional driving force against the socket portion to crush lock the screw head at the selected angle relative to the cup.

6 Claims, 7 Drawing Sheets

ACETABULAR CUP HAVING CAPPED POLYAXIAL LOCKING SCREWS

CROSS REFERENCE A TO RELATED APPLICATION

This application is a continuation-in-part of application U.S. Ser. No. 08/632,560, entitled "An Acetabular Cup Having Polyaxial Locking Screws", filed Apr. 15, 1996 now U.S. Pat. No. 5,725,588.

BACKGROUND OF THE INVENTION

1. Field of the Invention

This invention relates generally to a replacement hip implant assembly, and more specifically to an acetabular cup having a plurality of tapered holes therein for receiving polyaxial locking screws and coupling elements, such that the screws may be inserted into the adjacent bone at a wide range of angles.

2. Description of the Prior Art

Hip implant devices, which are utilized to replace corrsponding degenerated joints, generally include an outer metal cup (acetabular cup), and inner polymer or ceramic cup, a metal or ceramic ball, and a femoral post. The outer metal cup is implanted into the acetabulum (the socket portion of the pelvis), and secured therein by a variety of means, some of which are described hereinbelow. The inner polymer or ceramic cup seats within the outer metal cup and has a smooth semi-spherical interior conformation for receiving the metal or ceramic ball. The ball is smooth so as to provide low-friction polyaxially rotatability within the semi-spherical interior of the inner cup. The ball is also coupled to the top of the femoral post, which extends into the top of the femur to complete the coupling of the hip to the femur, while permitting rotation of the artifial joint.

There are a number of prosthetic hip devices which have been disclosed in the art which include the elements set forth above in various embodiments. The various embodiments disclose a spectrum of means for securing the acetabular cup to the pelvis. Some teach integral projections extending from the exterior surface of the cup-shaped body which provide anchoring for the element within the surrounding bone. European Patent Application No. 13,863, published on Jun. 8, 1980 describes such a device. The cup of this reference is anchored to the bone by a central pin and a number of other pins distributed over the surface of the cup. The pins have sawtooth notches along their length and are inserted into pre-drilled holes in the bone. Similarly, European Patent Application No. 211,169 published Feb. 25, 1987, discloses an acetabular cup which includes an external boss protruding from the outer surface of the cup to fit into a pre-drilled hole in the acetabulum.

An advance over fixed and integral anchoring projections is illustrated in U.S. Pat. No. 4,828,565 wherein the acetabular shell includes a pair of outwardly projecting elements which are fixed, but through which screws may be passed to further secure the cup in the bone.

The use of screws alone to anchor the acetabular cup in the surrounding bone is described in U.S. Pat. Nos. 3,939, 497 and 4,685,923 in which a series of radially arranged pegs may be selectively projected outwardly through the wall of the cup into the surrounding bone.

In each of the devices described above, the integral anchoring projections and/or the selectively introduceable screws, the entrance angles of the securing means are rigidly predetermined. As it is desirable to provide the surgeon with the freedom to choose the entrance angle of the screw to best suit the individual conformation of the surrounding bone on a patient-by-patient basis, U.S. Pat. No. 4,792,337 provides an acetabular cup having countersunk holes and screws having rounded heads, such that the orientation of the screws may be varied with respect to the cup and each other.

While it is a substantial gain over the previous designs to provide for variability in screw entrance angle, a common concern with screws being implanted into bone is that the screws may dislocate and begin a process known as "pull-out". This is an especially important problem in conjunction with acetabular cups, wherein dislocated screws often impede the rotational motion of the device and/or provide a wearing impetus to erode the low friction surfaces at the motion interface.

There are no presently available screw plate assemblies which present a flush surface and provide for means of preventing both screw pull-out from the bone and screw backout, while simultaneously providing for a wide range of angulation for the bone screws.

It is therefore, an object of the present invention to provide a new and novel acetabular cup and anchoring screw design which allows for polyaxial entrance of the screw into the surrounding bone.

It is also an object of the present invention to provide an orthopaedic implant which has a simple and effective mechanism for locking the bone screw to the acetabular cup.

Other objects of the present invention not explicitly stated will be set forth and will be more clearly understood in conjunction with the descriptions of the preferred embodiments disclosed hereafter.

SUMMARY OF THE INVENTION

The preceding objects of the invention are achieved by the present invention which is a locking polyaxial screw and coupling element assembly for use in anchoring acetabular cups within surrounding bone tissue. The assembly comprises: an acetabular cup having a plurality of tapered holes; bone screws having semi-spherical heads; and corresponding two-piece interlocking coupling elements.

The acetabular cup of this invention is generally of a type which is well known in the art, having a semi-spherical exterior conformation for insertion into the prepared bone site, and a curvate interior wherein the inner cup of the device is disposed. The cup further includes a plurality of holes extending through the cup; each of the holes having an inner portion (closer to the interior of the cup) which is threaded and an outer portion which is axially tapered such that the outer portion of the hole narrows to the exterior surface.

The heads of the screws further comprise a recessed region such as a slot, phillips, star, or hexagonal recesses which are ideally suited for mating to an appropriate screw-driving tool. The recess, however, does not alter the exterior radially semi-spherical shape of the head.

The two-piece interlocking coupling elements each comprise a socket portion and a cap portion. The socket portion is designed with an interior semi-spherical volume, so that it may receive the semi-spherical head of a corresponding bone screw. The interior volume of the socket portion is open at both axial ends thereof. The exterior surface of the socket portion, at the bottom thereof, includes a first set of slots which extend upwardly from the opening so that the interior semi-spherical volume may be expanded or contracted by the application of a radial force. In addition, the exterior surface at the bottom is tapered so that it is narrower at the bottom than at a midpoint.

The upper exterior surface of the socket portion comprises a second set of slots, directed axially along the element to the midpoint, such that the upper opening of the socket element may expand and contract in accordance with the application of a radial force thereon. The exterior surface of this upper section of the socket portion is not tapered and is narrower than the widest taper position of the bottom of the socket portion. The upper section, however, does further include an outwardly extending annular lip at the uppermost axial position. This upper section is designed to be inserted into, and joined with, the cap portion of the coupling element.

The cap portion has a generally cylindrical shape, having an open bottom. The open bottom is inwardly tapered, forming an inwardly extending annular lip, so that as the upper end of the socket portion is inserted, its upper slots are narrowed. Once axially inserted beyond this taper, the upper section of the socket portion expands outward over the inwardly extending annular lip. The inwardly extending annular lip engages the outwardly extending lip of the socket portion so as to prevent disengagement of the two pieces. The socket portion is then permitted to slide into the cap portion, until the larger diameter of the tapered lower portion of the socket contacts the entrance of the cap portion.

The exterior surface of the cap portion is threaded, so that it may engage the threading of the inner portion of the corresponding hole in the acetabular cup itself. In addition, the top of the cap includes an opening so that a screw driving tool may directly engage the top of the screw.

The first step in the process of implanting this embodiment of the invention is to assemble the parts described above. (It is intended that this assembly occur at the manufacturing site, and not be the responsibility of the surgical staff). The semi-spherical head of the screw is inserted into the interior volume of the socket portion, and held in place by the interference fit of the maximum diameter of the head with the unexpanded openings at the top and bottom of the element. The head is inserted from the bottom, and more specifically by applying a pressure which causes the bottom opening to expand to receive the head into the volume.

Once the screw head is inserted, the upper end of the socket portion is inserted into the opening of the cap portion. This insertion causes the top of the socket portion to contract inward slightly until the annular lips of each portion engage one another. The socket portion and the cap portion are thereby joined loosely so that each may slide and rotate relative to one another.

The surgeon then positions the acetabular cup in the hip socket and aligns the entry points for the screws. The next step is to pre-drill the holes into the bone at the desired angle, into which the screws will be inserted. With the cup in place, the screws (with the corresponding socket and cap portions in place on the head of each screw) are inserted through the holes, and into the bone. The coupling element provides access to the screw head for driving it into the bone. At all times during this insertion, the head of the screw is loosely retained within the coupling element, so that coupling element may polyaxially angulate relative to the screw, within a range of angles defined by the diameter of the neck of the screw and the bottom opening of the socket portion.

As the screw is inserted into the bone, at the desired angle, the socket portion of the coupling element angulates so that the tapered bottom portion thereof seats into the tapered portion of the hole in the cup. Continued driving of the screw into the bone, and therefore the socket portion of the coupling element deeper into the tapered portion of the hole, causes the first set of slots in the bottom end of the socket portion to narrow, thus causing the head of the screw to be crush locked to the coupling element. The cap portion of the coupling element is then threadably inserted into the threaded inner portion of the hole, locking the coupling element in the hole, and further driving the socket portion into the hole.

In a potential variation of this embodiment, the interior surface of the cap portion includes a slight narrowing taper so that as the cap is threaded downward into the hole in the cup, the upper slots of the socket portion are also narrowed, further increasing the crush locking effect on the head of the screw.

DETAILED DESCRIPTION OF THE PREFERRED EMBODIMENT

While the present invention will be described more fully hereinafter with reference to the accompanying drawings, in which particular embodiments and methods of fabrication are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope. Like numbers refer to similar features of like elements throughout.

Figure 1:
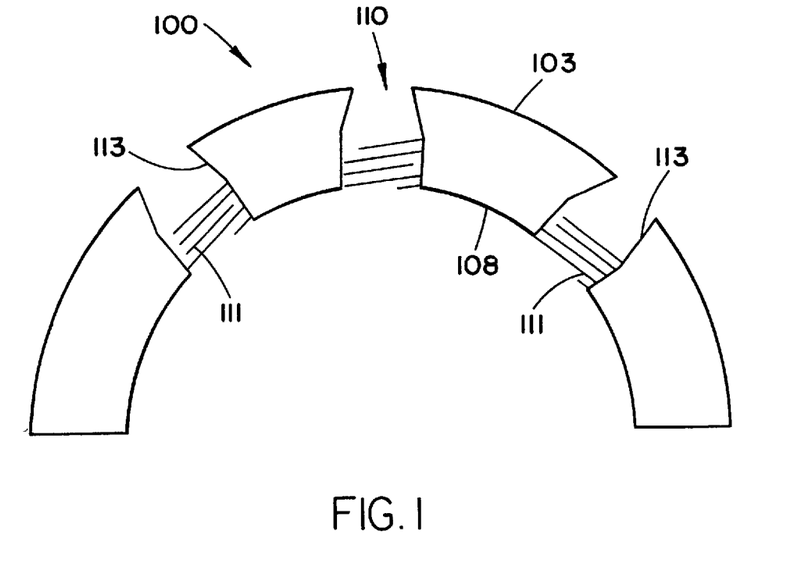
FIG. 1 is a side cross-section view of an acetabular cup which is an aspect of the present invention.
Figure 2:
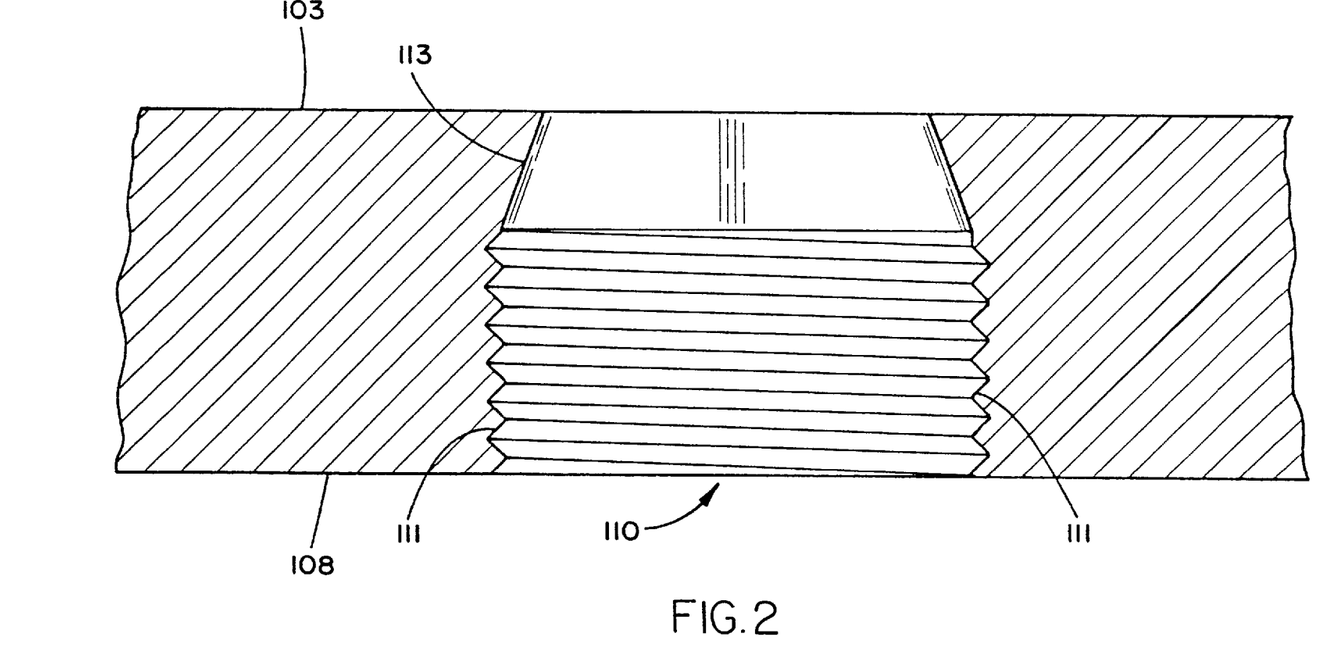
FIG. 2 is a side cross-section view of a receiving hole in the acetabular cup of the present invention.

Referring now to FIGS. 1 and 2, an acetabular cup 100 of the present invention is shown, respectively, in a side cross-section view, the cross-section being taken in a diametric plane, and a side cross-section of one of the axially tapered holes 110 therein. The cup 100 may be constructed of any suitably biocompatible material which has the structural strength and durability to withstand the cyclical loading associated with long term fixation in the hip. Materials which would be suitable for such applications include titanium alloys and steels. These materials have enhanced mechanical properties including fatigue endurance and tensile strength, as compared with other materials.

The cup 100 comprises inner and outer surfaces 108 and 103, respectively, said inner surface 108 being concave and the outer surface 103 being convex. A second cup shaped insert (not shown) is often affixed within the acetabular cup 100, the inner surface of this second cup being the bearing surface against which the ball head of the femoral post portion of the artificial hip joint rotates.

A plurality of holes 110, having a smooth tapered outer portion 113 and a constant diameter threaded inner portion 111, extend fully through the cup 100. Each of the holes 110 is ideally suited for receiving therethrough a bone screw for affixing the cup to the bone of the hip socket.

Figure 3:
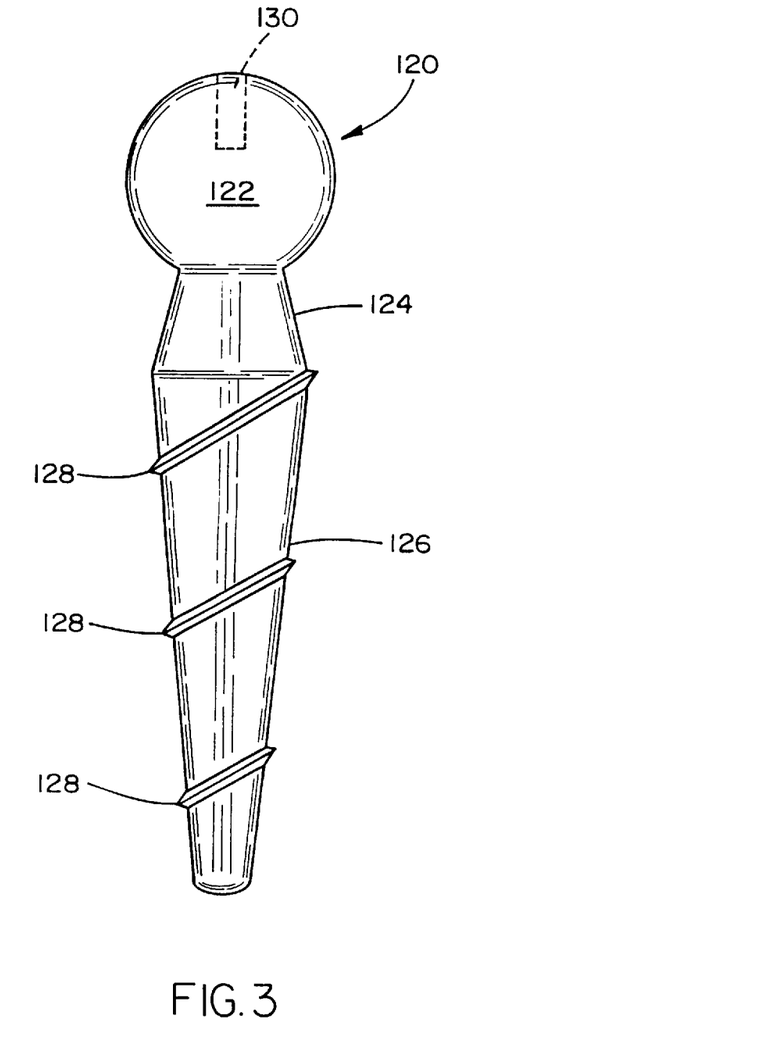
FIG. 3 is a side view of a bone screw of the present invention.

Referring now to FIG. 3, a screw of a type which is ideally suited for securing the acetabular cup 100 of this invention to the hip of the patient is shown in a side view. The screw 120 comprises a head portion 122, a neck 124, and a shaft 126. In FIG. 3, the shaft 126 is shown as having a tapered shape with a high pitch thread 128. It shall be understood that a variety of shaft designs are interchangeable with the present design. The specific choice of shaft features, such as thread pitch, or shaft diameter to thread diameter ratio, or overall shaft shape, etc. should be made be the physician with respect to the conditions of the patient's bone, however, this invention is compatible with a wide variety of shaft designs.

The head portion 122 of the screw 120 comprises a semi-spherical shape, which has a recess 130 in it. It is understood that the semi-spherical shape is necessarily is a section of a sphere, greater in extent than a hemisphere, and exhibits an external contour which is equidistant from a center point of the head. In a preferred embodiment, the major cross-section of the semi-spherical head 122 (as shown in the two dimensional illustration of FIG. 3) includes at least 270 degrees of a circle.

The recess 130 defines a receiving locus for the application of a torque for driving the screw 120 into the bone. The specific shape of the recess 122 may be chosen to cooperate with any suitable screwdriving tool. For example, the recess 130 may comprise a slot for a flat-headed screwdriver, a crossed recess for a phillips head screwdriver, a hexagonally shaped hole for receiving an allen wrench, or most preferably, a threading for receiving a correspondingly threaded post. It is further preferable that the recess 130 be co-axial with the general elongate axis of the screw 120, and most particularly with respect to the shaft 126. Having the axes of the recess 130 and the shaft 126 co-linear facilitates the step of inserting the screw 120 into the bone.

The semi-spherical head portion 122 is connected to the shaft 126 at a neck portion 124. While it is preferable that the diameter of the shaft 126 be less than the radius of the semi-spherical head 122, it is also preferable that the neck 124 of the screw 120 be narrower than the widest portion of the shaft 126. This preferable dimension permits the screw to be inserted at a variety of angles while still permitting the specific coupling element to be screwed into the appropriate hole 110 of the cup 100 and remain coupled to the head 122.

Figure 4:
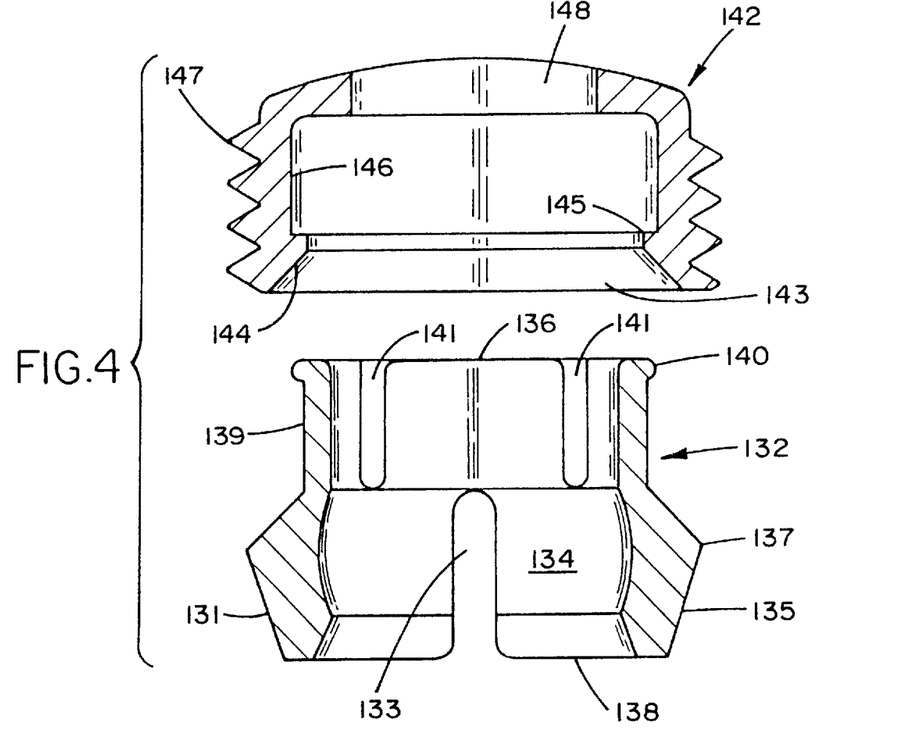
FIG. 4 is a side view of a two-piece interlocking coupling element of the present invention.

Referring now also to FIG. 4 the two portions which form the two-piece interlocking coupling element of the present invention are shown in a side cross-section view. Phantom lines show the interior structure of the elements along the diametrical cross section. With specific reference to the socket portion 132, the coupling element comprises a roughly cylindrical shape having an interior volume 134 in which the semi-spherical head 122 of the screw 120 is disposed. The interior volume 134 is open at the top 136 of the socket portion 132 and at the bottom thereof 138. The lower section 131 of the socket portion 132 comprises a set of slots 133 which extend vertically from the bottom 138 of the socket portion 132 to a position above the maximum diameter of the semi-spherical interior volume 134. These slots 133 permit the interior volume to expand and contract in accordance with the application of a radial force thereon. The external surface 135 of the lower section 131 of the socket portion 132 is tapered such that the narrowest part of the lower section 131 is at the bottom 138.

The upper section 139 of the socket portion 132 has a generally constant diameter, which is less than the diameter at the uppermost position 137 of the taper of the lower section 131. A second set of vertical slots 141 are provided in this upper section 139 so that it may also expand and contract in accordance with radial forces applied thereto. In addition, the uppermost end of this upper section 139 comprises an outwardly extending annular lip 140.

The cap portion 142 of the coupling element comprises an opening 143 in the bottom thereof, having an inwardly tapered entrance surface conformation 144. As the upper section 139 of the socket portion 132 is inserted into the opening 143 in the cap portion 142, the taper 144 of the opening 143 provides an inwardly directed force which causes the upper section 139 to contract (causes the slots 141 to narrow). This tapered entrance 144 opens to form an annular lip 145 which is useful for engaging and retaining the annular lip 140 of the upper section 139 of the socket portion 132. The interior surface 146 of the cap portion has a constant diameter, therein permitting the inserted upper section 139 of the socket portion 132 to slide and rotate relative to the cap portion 142.

The exterior surface of the cap portion 142 comprises a threading 147 which is designed to engage the threading 111 in the upper portion of the corresponding hole 110 or 112. In addition, the cap portion 142 comprises an axial hole 148 through which a surgeon may insert a screw driving tool to access the head of the screw which is positioned in the interior volume 134 of the socket portion 132.

Figure 5:
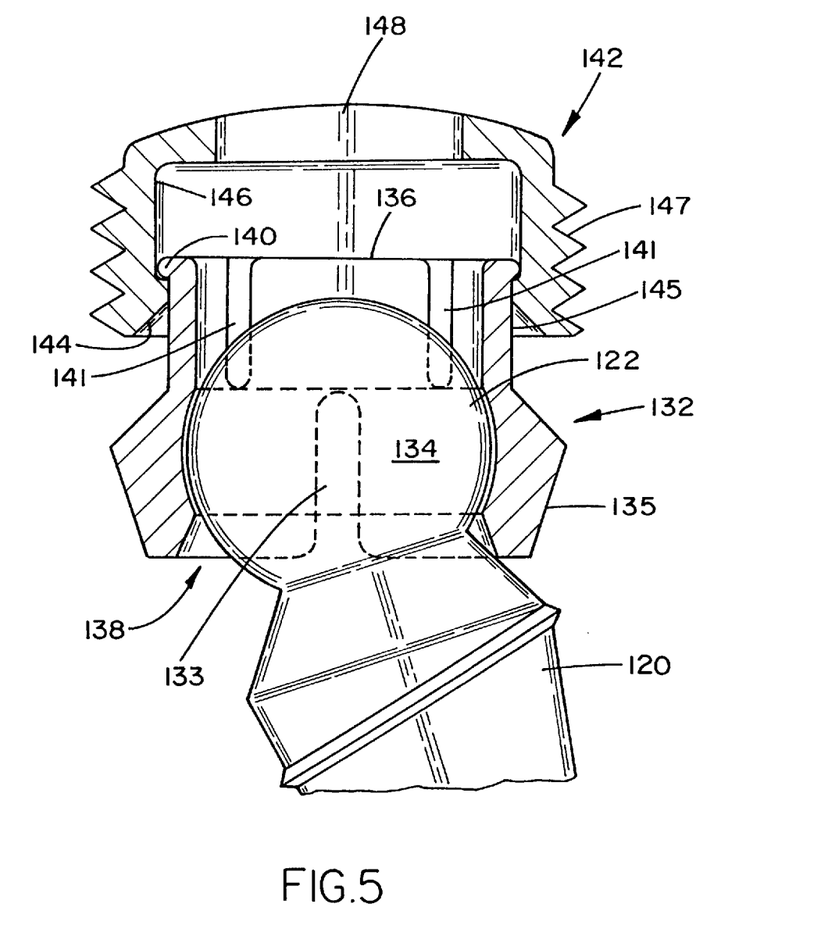
FIG. 5 is a side cross-section view of a partially assembled screw and interlocking coupling element of the present invention.

More particularly, with respect to the disposition of the head 122 of the screw 120 in the socket portion 132, and with respect to FIG. 5, the top 136 of the socket portion 132 is inserted into the opening in the cap portion 142 until the annular lip 140 of the socket 132 seats into the cap 142. The screw 120 is loosely held within the socket 132, which is, in turn, loosely retained within the cap 142.

Figure 6:
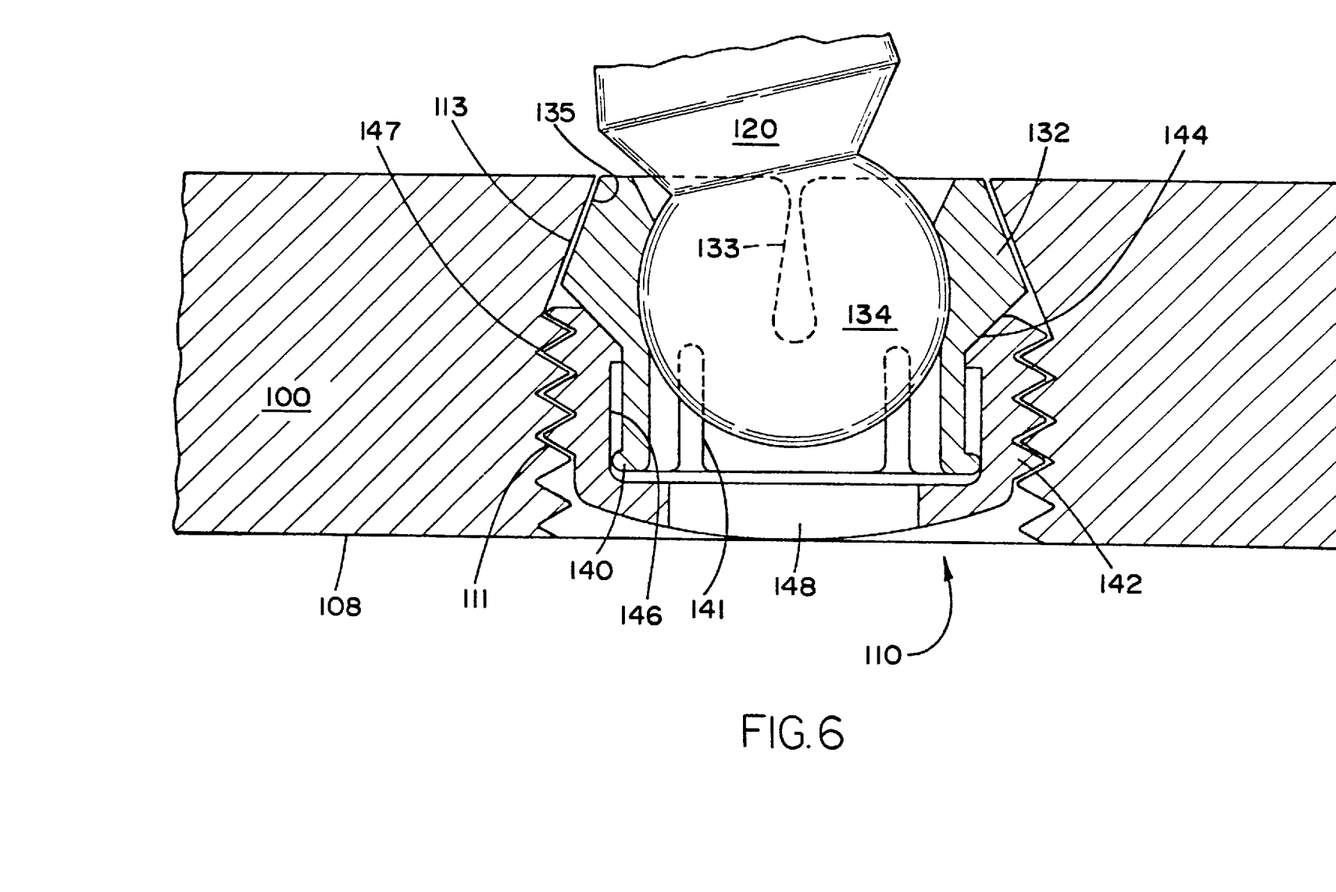
FIG. 6 is a side cross-section view of a fully assembled embodiment of the present invention incorporating, the two-piece interlocking coupling elements as shown in FIG. 4.

Referring now to FIG. 6, in which the fully assembled and inserted screw and coupling element are shown in side cross-section view, in the hole 110 in the cup, the implantation of this embodiment is described. The cup 100 is positioned in the hip socket, against the bones to which it is to be immobilized. A drill is used to pre-form holes into which the bone screws 120 are to be inserted (at the desired angulation). The screw 120, which has already been coupled with the two-piece interlocking coupling element polyaxially mounted to the semi-spherical head, is is then inserted and driven into the bone by use of the appropriate screw driving tool. As the screw 120 is driven deeper into the bone, the coupling element mounted to the head of the screw begins to enter the hole 110 of the cup 100. As the coupling element enters the hole 110, the tapered exterior surface 135 of the socket portion 132 seats against the tapered portion 113 of the hole 110. Continued driving of the screw into the bone causes the slot 133 in the bottom of the socket portion 132 to narrow, thus causing the interior volume 134 of the socket portion 132 to crush against the head 122 of the screw 120.

The cap portion 142 of the coupling element may then be threadably advanced into the inner portion 111 of the hole 110. As it is advanced, the upper annular lip 140 of the socket portion 132 slides upwardly along the inner surface 146 of the cap 142 until the bottom tapered opening 144 contacts the widened taper position of the socket portion 132. Continued advancement of the cap portion 142 provides further advancement of the socket portion 132 into the tapered portion 113 of the hole 110, thereby increased locking pressure within the interior volume 134 against the head 122.

Figure 7:
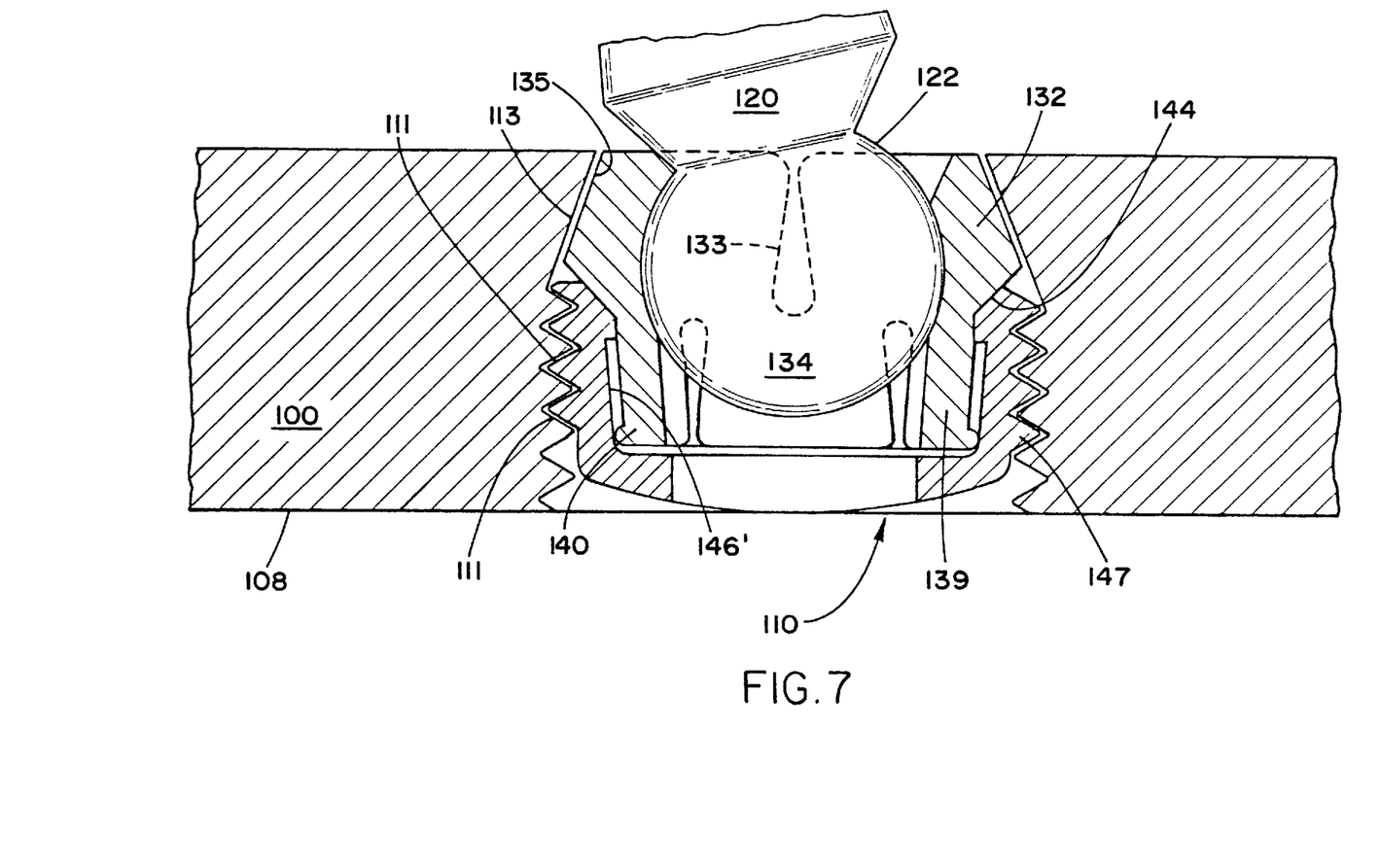
FIG. 7 is a side cross-section view of a fully assembled embodiment of the present invention incorporating, a variation of the two-piece interlocking coupling elements as shown in FIG. 4.

Referring to FIG. 7, a variation of the above device is shown in a similar cross-section view. In this embodiment, the inner surface 146' of the cap portion 142 is tapered inwardly in the vertical direction so that the advancement of the cap portion 142 along the threading 111 of the hole 110 causes the annular lip 140 to be compressed inwardly. This causes the slots 141 of the upper section 139 of the socket portion 132 to narrow. This may be utilized to further clamp the interior volume 134 against the head 122 of the screw 120. Once screwed into the cup 100, and locked down, the cap portion 142 of the coupling element and the inner surface 108 of the cup present a flush surface.

While there has been described and illustrated acetabular cups having polyaxial fixation means, it will be apparent to those skilled in the art that variations and modifications are possible without deviating from the broad spirit and principle of the present invention which shall be limited solely by the scope of the claims appended hereto.

We claim:

1. An acetabular cup assembly having polyaxial locking anchoring screws for securing said cup within a recess of surrounding bone, comprising:

an acetabular cup having at least one through hole, said through hole having an inner threaded portion and an outer tapered portion;

at least one bone screw, said bone screw having a semi-spherical head portion and a shaft; and at least one coupling element, comprising a socket portion having a semi-spherical interior volume, upper and lower sections, and vertical slots formed on corresponding ones of said upper and lower sections, at least one of said slots rendering said interior volume expandable and contractable, said lower section having a tapered exterior surface for seating against the outer tapered portion of said through hole such that forceable advancement of socket portion into the tapered portion of the through hole causes the at least one of said slots to narrow whereby the semi-spherical interior volume contracts, and a cap portion having an opening in a bottom thereof and an interior chamber extending upwardly therefrom for joining with, and slideably retaining therein, the upper section of said socket portion, and exterior threading which is mateable with the threading of the inner portion of the through hole, wherein said semi-spherical head portion is rotationally freely mounted within the semi-spherical interior volume of the socket portion of the coupling element prior to insertion, and whereby the insertion of the shaft of the bone screw and the coupling element into the through hole, and the insertion of said shaft of the bone screw into the surrounding bone at a selected angle within a predetermined range of angles including non-perpendicular angles to the plate, causes the tapered exterior surface of the socket portion to seat and to be forceably advanced against the outer tapered portion of the through hole such that the semi-spherical head of the screw is locked within the contracted semi-spherical interior volume, and whereby threaded advancement of the cap portion into said through hole provides additional forceable advancement of the socket portion against the tapered portion of the through hole.

2. The assembly as set forth in claim 1, wherein the head portion of said screw comprises a recess to which a screw-driving tool is matable for inserting said screw through the through hole and into the surrounding bone.

3. The assembly as set forth in claim 2, wherein said socket portion comprises an opening in said upper section thereof, through which a screwdriving tool may be inserted, and which may be aligned with the recess in the head of the screw.

4. The assembly as set forth in claim 3, wherein said cap portion comprises an opening in a top thereof, aligned with the opening in the upper section of the socket portion, through which said screwdriving tool may be inserted, and which top surface recess may be aligned with the recess in the head of the screw.

5. The assembly as set forth in claim 1, wherein said socket portion further comprises a substantially constant diameter upper section having an outwardly annular extending lip at an extreme end thereof, wherein said opening in the bottom of the cap portion comprises an inwardly directed annular lip, and wherein at least one of said vertical slots in the upper section of said socket portion renders the upper section thereof to be expandable and contractable such that the upper section of the socket portion may be forceably inserted into the opening in the bottom of the cap portion so that it may be retained in the interior chamber therein by mutual interference engagement of the inwardly directed annular lip of the cap portion and the outwardly extending annular lip of the socket portion.

6. The assembly as set forth in claim 5, wherein the interior chamber of the cap portion comprises a tapered surface such that advancement thereof into the through hole causes an inwardly directed force against the upper section of the socket portion, therein causing the at least one of said vertical slots in the upper section to narrow and causes the upper section to contract and further lock the head of the screw within the interior semi-spherical volume of the socket portion.

* * * * *